US00PP33616P2

(12) United States Plant Patent
O'Connell

(10) Patent No.: US PP33,616 P2
(45) Date of Patent: Nov. 2, 2021

(54) ***ECHEVERIA* PLANT NAMED 'PINK DIAMOND'**

(50) Latin Name: *Echeveria hybrida*
Varietal Denomination: Pink Diamond

(71) Applicant: Altman Specialty Plants, Inc, Vista, CA (US)

(72) Inventor: Renee O'Connell, Escondido, CA (US)

(73) Assignee: Altman Specialty Plants Inc., Vista, CA (US)

( * ) Notice: Subject to any disclaimer, the term of this patent is extended or adjusted under 35 U.S.C. 154(b) by 0 days.

(21) Appl. No.: 17/130,625

(22) Filed: Dec. 22, 2020

(51) Int. Cl.
*A01H 5/12* (2018.01)
*A01H 6/32* (2018.01)

(52) U.S. Cl.
USPC ..... Plt./373
CPC ..... *A01H 6/32* (2018.05)

(58) Field of Classification Search
USPC ..... Plt./373
CPC ..... A01H 6/32; A01H 5/12
See application file for complete search history.

*Primary Examiner* — Keith O. Robinson
(74) *Attorney, Agent, or Firm* — Cassandra Bright

(57) ABSTRACT

A new and distinct plant of *Echeveria hybrida* named 'Pink Diamond' is disclosed, characterized by robust growth on plants forming a compact rosette of geometric pink leaves with hyaline margins. Plants produce foliage with more pink coloration in cool temperatures, and also maintain a pink foliar color in warmer temperatures as well. *Echeveria* is a popular genus, typically produced as container plants for the patio or as landscape plants.

2 Drawing Sheets

Latin name of the genus and species: *Echeveria hybrida.*
Variety denomination: 'PINK DIAMOND'.

BACKGROUND OF THE INVENTION

The new cultivar *Echeveria* 'Pink Diamond', is the product of chance discovery by the inventor. The new variety was discovered as a whole plant, naturally occurring mutation of the parent variety, the unpatented *Echeveria hybrida* cultivar known as 'Lola'. The discovery was made during November of 2015, in Vista, Calif., at a commercial greenhouse.

Asexual reproduction of the new cultivar 'Pink Diamond' was first performed in Vista, Calif., at a commercial greenhouse, by vegetative offsets in March of 2016. *Echeveria* 'Pink Diamond' has since produced at least 10 generations and has shown that the unique features of this cultivar are stable and reproduced true to type.

SUMMARY OF THE INVENTION

The cultivar 'Pink Diamond' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'PINK DIAMOND'. These characteristics in combination distinguish 'PINK DIAMOND' as a new and distinct *Echeveria* cultivar:

1. *Echeveria* 'Pink Diamond' forms compact rosettes of geometric pink leaves with hyaline margins, a combination not encountered often in the market of "pink" succulents.
2. *Echeveria* 'Pink Diamond' will become more pink with cool temperatures, but always retains a pink coloration, whereas many other "pink" succulents found in today's market only blush pink in cool temperatures and are usually silvery blue or white at other times.
3. *Echeveria* 'Pink Diamond', an attractive, compact pink rosette, is ideal for use as an accent in groups of blue or green *Echeverias*, or as an eye-catching accent in a decorative grouping of succulents, particularly those of orange or yellow tones.
4. *Echeveria* 'Pink Diamond' is a robust grower, not displaying the problematic tendencies encountered with many of the other "pink" *Echeverias* with genetic lines of *Echeveria lauii* and *Echeveria agavoides* 'Romeo' (unpatented).

PARENTAL COMPARISON

Plants of the new cultivar 'Pink Diamond' are similar to plants of the parent in most horticultural characteristics. However, plants of the new cultivar 'Pink Diamond' differ in the following:

1. *Echeveria* 'Pink Diamond' forms pink rosettes, with a slight upswept tendency to the leaves, whereas *Echeveria* 'Lola' forms alabaster rosettes, blushed in violet during cooler temperatures.
2. *Echeveria* 'Pink Diamond' is relatively pathogen free, as is *Echeveria* 'Lola'.
3. Although *Echeveria* 'Lola' has the same hyaline margins as *Echeveria* 'Pink Diamond, *Echeveria* 'Pink Diamond' exhibits a greater contrast between the rosette color and the hyaline margin than does *Echeveria* 'Lola'.

COMMERCIAL COMPARISON

The new cultivar 'Pink Diamond' can be compared to the commercial variety *Echeveria* 'Cubic Frost', U.S. Plant Pat. No. 27,527. Plants of the new cultivar 'Pink Diamond' differ in the following:

1. *Echeveria* 'Pink Diamond' forms compact pink rosettes of geometric leaves, whereas *Echeveria* 'Cubic Frost' has upswept, longer pink tubular leaves arranged in a rosette.
2. *Echeveria* 'Pink Diamond' exhibits hyaline margins whereas *Echeveria* 'Cubic Frost' does not have hyaline margins.
3. *Echeveria* 'Pink Diamond' produces leaves that are pink in color, whereas *Echeveria* 'Cubic Frost' produces leaves that are of a more frosted pink due to the glaucous covering.

The new cultivar 'Pink Diamond' can be compared to the unpatented *Echeveria shaviana* 'Pink Frills'. Plants of the new cultivar 'Pink Diamond' are similar to *Echeveria* 'Pink Frills' in most horticultural characteristics. However, plants of the new cultivar 'Pink Diamond' differ in the following:

1. *Echeveria* 'Pink Diamond' forms upswept rosettes of pink leaves, whereas *Echeveria shaviana* 'Pink Frills' forms rosettes of lateral leaves of powdery lilac with pink margins.
2. *Echeveria* 'Pink Diamond' exhibits concentric, roughly spatulate leaves whereas, *Echeveria shaviana* 'Pink Frills' displays longer leaves with finely crenulate margins towards the apex of the leaf.
3. *Echeveria* 'Pink Diamond' exhibits pink leaves with highly contrasting hyaline margins, whereas *Echeveria shaviana* 'Pink Frills' does not display a hyaline leaf margin.
4. *Echeveria* 'Pink Diamond' is a more robust grower than is *Echeveria shaviana* 'Pink Frills', particularly as *Echeveria* 'Pink Diamond' does not display the seasonal dormancy that seems to cause *Echeveria shaviana* 'Pink Frills' to be prone to lethal fungal diseases.

BRIEF DESCRIPTION OF THE PHOTOGRAPHS

The photographs were taken using conventional techniques and equipment. While the colors in these photographs may display variances of color as compared to the living cultivar, due to LRV (light reflectance value), they are as accurate as possible using conventional photographic techniques. Colors in the photographs may appear to differ slightly from the color values cited in the botanical description, which accurately describe the colors of new *Echeveria* 'Pink Diamond'. Plants photographed are approximately 4 months from a rooted cutting.

DETAILED BOTANICAL DESCRIPTION

Figure 1:
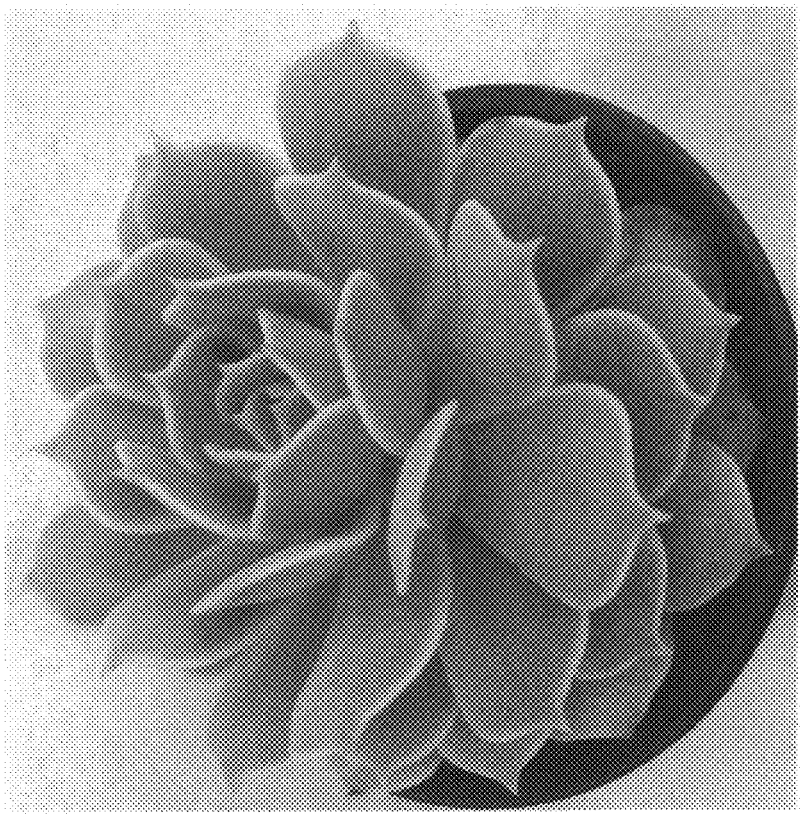
FIG. 1 illustrates in full color the plant being described of *Echeveria* 'Pink Diamond', grown in a greenhouse (approximately 2000-2500 foot candles) in Vista, Calif.
Figure 2:
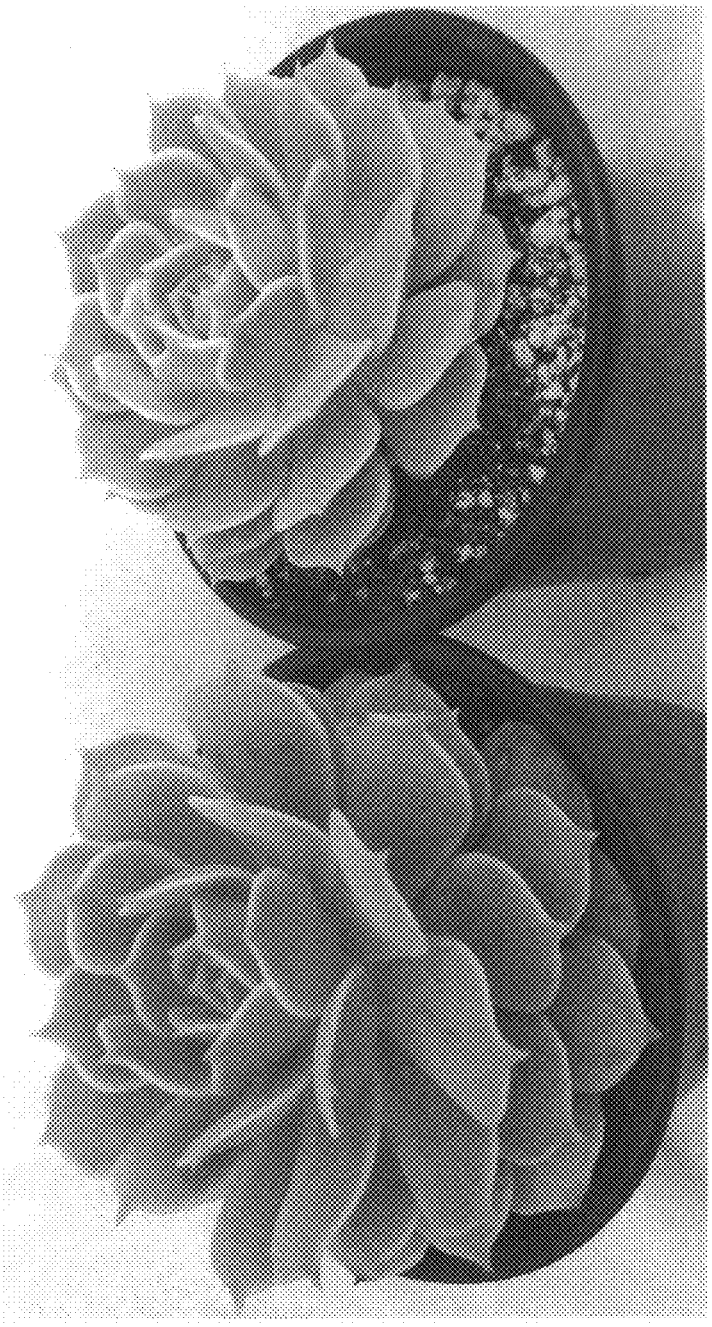
FIG. 2 illustrates in full color a plant of *Echeveria* 'Pink Diamond', on the left in the figure, and a plant of the comparator 'Lola', on the right in the figure. Both plants were grown in a greenhouse (approximately 2500 foot candles) in Vista, Calif. under identical conditions.

In the following description, color references are made to The Royal Horticultural Society Colour Chart, 2007, except where general terms of ordinary dictionary significance are used. The following observations and measurements describe 'Pink Diamond' plants in a commercial greenhouse in Vista, Calif. Temperatures ranged from 2° C. to 38° C. night and day. No artificial light, photoperiodic treatments or chemical treatments were given to the plants. Natural light conditions were approximately 2500 fc of light. Measurements and numerical values represent averages of typical plant types.

Botanical classification: *Echeveria hybrida* 'PINK DIAMOND'.

PROPAGATION

Type of propagation typically used: Terminal vegetative cuttings.

Time to initiate roots: About 11 days at approximately 24° C.

Root description: Fibrous.

PLANT

Age of plant described: Approximately 4 months from a cutting.

Container size of the plant described: 12 cm.

Growth habit: Moderately dense, symmetrical rosette.

Height: Approximately 9 to 12 cm to top of highest leaf.

Plant spread: Approximately 12 cm.

Growth rate: Moderate to rapid.

Branching characteristics: Rosette forming, no branching.

FOLIAGE

Leaf:

*Arrangement.*—Rosulate.

*Quantity.*—55 to 70 per plant.

*Average length.*—Average range 3.8 to 4.5 cm.

*Average width.*—2.5 cm.

*Thickness.*—9 to 10 mm.

*Shape of blade.*—Blunt spatulate.

*Apex.*—Broad, near flat, then apiculate. Slightly sharp.

*Base.*—Truncate.

*Margin.*—Entire.

*Aspect.*—Moderately concave.

*Texture of top surface.*—Glabrous.

*Texture of bottom surface.*—Glabrous.

*Appearance of top surface.*—Matte, slightly glaucous. Hyaline margin.

*Appearance of bottom surface.*—Matte, slightly glaucous. Hyaline margin.

*Color.*—Young foliage upper side: Near RHS Greyed-Green 190C, heavily flushed or completely flushed Greyed-Purple 186C. Margin hyaline, Yellow-White 158C flushed Greyed-Purple 186D. Apical point colored near Red-Purple 58A. Young foliage, under side: Near RHS Greyed-Purple 186D, flushed 186C. Margin hyaline, Yellow-White 158C flushed Greyed-Purple 186D. Apical point colored near Red-Purple 58A. Mature foliage upper side: Near RHS Greyed-Green 190C completely covered in Greyed-Purple N187D. Margin hyaline, Yellow-White 158C flushed Greyed-Purple 186D. Apical point colored near Red-Purple 58A. Mature foliage, under side: Near Greyed-Purple N187C flushed 186C and 186B. Margin hyaline, Yellow-White 158C flushed Greyed-Purple 186D. Apical point colored near Red-Purple 58A.

*Venation.*—There is no visual appearance of venation.

FLOWER

Natural flowering season: Approximately Spring until Fall in Southern California.

Inflorescence type and habit: Raceme.

Flower longevity on plant: 10 to 20 days depending upon ambient temperatures.

Quantity of flowers per inflorescence: 3 to 5 open flowers and 3 buds.

Total inflorescence size:

*Height*.—Approximately 10 to 15 cm.

*Width*.—Approximately 6 to 7 cm.

Corolla:

*Arrangement*.—Pentagonal, tightly held, fused at base.

*Size*.—Diameter: Average 1.4 cm. Length: 1.8 cm.

Petals:

*Quantity*.—5.

*Length*.—Approximately 1.7 cm.

*Width*.—Approximately 7 mm.

*Margin*.—Entire.

*Shape*.—Lanceolate.

*Apex*.—Acute.

*Base*.—Fused at bottom 10% to 20% of length.

*Texture*.—Glabrous, all surfaces.

*Color*.—When opening: Outer surface: Near RHS Orange-Red N34B, apex Greyed-Red 182B, base Yellow 8D. Inner surface: Near RHS Green-Yellow 1C. Thin margin near Orange-Red N34A. Fully opened: Outer surface: Near RHS Red 50C, strongly flushed 50B with bright center streak 50A. Margins Yellow 11C. Inner surface: Near RHS Yellow 11A, base 11C, upper half lightly flushed Red 50A.

*Color changes when aging*.—Outer surface: Near RHS Greyed-Red 182B. Inner surface: Near RHS Greyed-Red 181C.

Bud: (near opening):

*Shape*.—Broad conical.

*Length*.—Approximately 1.2 cm.

*Diameter*.—Approximately 8 mm.

*Color*.—Near RHS Orange-Red N34B, apex Greyed-Red 182B, base Yellow 8D.

Sepals:

*Length*.—7 mm.

*Width*.—5 mm.

*Margin*.—Entire.

*Shape*.—Deltate.

*Apex*.—Acute.

*Base*.—Truncate.

*Texture*.—Glabrous, upper and lower surfaces.

*Appearance*.—Shiny, upper and lower surfaces.

*Color*.—Outer: Near Greyed-Green 189A. Inner: Near Greyed-Green 189A. Thin margin near Red 50A.

Peduncle:

*Length*.—Average range 5 to 10 cm.

*Width*.—Approximately 6 mm.

*Strength*.—Strong.

*Texture*.—Glabrous.

*Color*.—Near RHS Greyed-Green 196D lightly flushed Greyed-Red 181D.

Pedicels:

*Length*.—Average 1.5 cm.

*Width*.—Approximately 3 mm.

*Strength*.—Moderately strong.

*Texture*.—Glabrous.

*Color*.—Near RHS Greyed-Red 182B.

Fragrance: None detected.

REPRODUCTIVE ORGANS

Stamens: (Androceium).

*Number*.—Most commonly 10.

*Filament length*.—Approximately 5 mm.

*Filament color*.—Near RHS Green-Yellow 1D.

*Anther length*.—1 mm.

*Anther color*.—Near RHS Yellow-Green N144B.

*Anther shape*.—Linear.

*Pollen*.—Not observed.

Pistil: (Gynoecium).

*Number*.—Average 5.

*Length*.—Approximately 7 mm.

*Style color*.—Near Yellow-Green 145C, flushed Yellow-Green 144C.

*Stigma*.—Shape: Linear. Color: Near RHS Greyed-Purple 183A. Ovary Color: Near RHS Yellow-Green 145D.

OTHER CHARACTERISTICS

Fruits and seeds: Not observed.

Temperature tolerance: Tolerates temperatures from approximately −2° C. to at least 35° C.

Disease/pest resistance: Resistance observed to fungal diseases common with overwatering of *Echeveria* plants. Neither resistance or susceptibility to other normal diseases and pests of *Echeveria* has been observed. The pathogen of the fungal diseases cause leafspot in *Echeveria* is unconfirmed. Potential pathogens include *Alternaria* spp., *Bipolaris cactivori, Botrytis* spp., *Cladosporium tenuissimum, Colletotrichum* spp. and *Cercospora* spp.

Drought tolerance: Tolerates at least 3 weeks of high temperatures without supplemental water, showing no serious damage to plant.

What is claimed is:

1. A new and distinct cultivar of *Echeveria* plant named 'PINK DIAMOND' as herein illustrated and described.

* * * * *